United States Patent [19]
Lin et al.

[11] Patent Number: 6,140,547
[45] Date of Patent: Oct. 31, 2000

[54] ISOMERIZATION OF HYDROCARBONS

[75] Inventors: Fan-Nan Lin, Bartlesville, Okla.; Edgar D. Davis, Borger, Tex.

[73] Assignee: Phillips Petroleum Company, Bartlesville, Okla.

[21] Appl. No.: 09/203,081

[22] Filed: Dec. 1, 1998

[51] Int. Cl.⁷ .............................. C07C 5/13; C10G 35/06
[52] U.S. Cl. ................... 585/743; 585/734; 585/738; 585/739; 585/745; 585/747; 585/748; 585/746; 585/750; 208/139
[58] Field of Search ...................... 585/734, 738, 585/739, 748, 743, 745, 747, 746, 750; 208/139

[56] References Cited

U.S. PATENT DOCUMENTS

| | | | |
|---|---|---|---|
| 2,945,910 | 7/1960 | Peterson ............................ | 260/683.74 |
| 3,158,662 | 11/1964 | Reichle et al. ..................... | 260/683.75 |
| 3,192,286 | 6/1965 | Houston et al. .................... | 260/683.73 |
| 5,474,964 | 12/1995 | Wu et al. ............................ | 502/326 |
| 5,557,029 | 9/1996 | Lin et al. ............................ | 585/739 |
| 5,654,247 | 8/1997 | Lin et al. ............................ | 502/53 |

*Primary Examiner*—Walter D. Griffin
*Assistant Examiner*—Tam M. Nguyen
*Attorney, Agent, or Firm*—Reece A. Scott

[57] ABSTRACT

An isomerization process for converting an isomerization feed stream containing alkanes having about 4 carbon atoms to about 10 carbon atoms per molecule and cycloalkanes having about 5 carbon atoms to about 10 carbon atoms per molecule to at least one product hydrocarbon isomer. The isomerization feed stream, which contains at least one feed hydrocarbon and hydrogen, is contacted in an isomerization zone at effective isomerization conditions with a catalyst where deactivation of such catalyst occurs in the isomerization zone. The isomerization process includes the presence of an additive in the isomerization feed stream. The concentration of the additive is sufficient to alleviate or diminish the deactivation of the catalyst and to maintain a substantially constant conversion of the at least one feed hydrocarbon to the at least one product hydrocarbon isomer at effective isomerization conditions.

27 Claims, No Drawings

ISOMERIZATION OF HYDROCARBONS

BACKGROUND OF THE INVENTION

The present invention relates to an isomerization process and the prevention of the deactivation of an isomerization catalyst used in such process.

Isomerization of normal alkanes, i.e., normal paraffins, is widely used in refinery processes for the upgrading of lower-valued hydrocarbons to hydrocarbons of higher value. In recent years there has been an increased interest in the isomerization of normal alkanes, having about 4 carbon atoms to about 10 carbon atoms, to isoalkanes, particularly the isomerization of normal butane to isobutane, and also, normal hexane to 2,2-dimethylbutane. Due to recent federal mandates concerning the vapor pressure of gasoline, it is desirable that high vapor pressure components, such as normal butane and normal hexane, are removed from the gasoline pool. However, upon the removal of such high vapor pressure components there must be some other use for such components. Thus, for example, butane isomerization is beneficial because isomerization of n-butane produces isobutane which can be used as a feedstock for various other refinery processes, such as alkylation and etherification, that produce high octane gasoline components.

The use of supported platinum catalysts (such as platinum on alumina) for isomerizing hydrocarbons, in particular normal alkanes to isoalkanes (such as n-butane to isobutane), is well known. A problem that is encountered in the isomerization of hydrocarbons is the rapid deactivation of the isomerization catalyst. There are believed to be a number of causes of catalyst deactivation. One such cause of catalyst deactivation is the formation and accumulation of high molecular weight hydrocarbons, such as $C_5$ to $C_8$ hydrocarbons, carbon, and/or coke, within the pores of the isomerization catalyst, particularly at the reaction sites, also referred to as acid sites, within the isomerization catalyst as well as on the isomerization catalyst surface. The formation and accumulation of such high molecular weight hydrocarbons causes a high rate of catalyst deactivation, a short run life of the catalyst, and an unsteady yield of hydrocarbon products.

In addition, impurities present in the feed stream contribute to a rapid decrease in catalyst activity. Pretreatment of the feed stream prior to isomerization to remove a major portion of these impurities is one option to help alleviate catalyst deactivation, but this route is expensive because additional equipment and operating costs are required. Also, the levels of these impurities in the feed stream may fluctuate, and pretreatment of the feed stream may not always be adequate.

Another option to alleviate the deactivation of isomerization catalysts by impurities is to operate the isomerization processes at relatively high hydrogen to hydrocarbon ratios and at relatively high temperatures. However, this route is also expensive and generally produces less amounts of the desirable isomer product(s) and more amounts of the undesirable by-products, mainly light gases which are formed by hydro-cracking of feed hydrocarbons.

SUMMARY OF THE INVENTION

It is an object of this invention to carry out the isomerization of an isomerization feed stream comprising an alkane(s) (i.e., paraffins) and/or a cycloalkane(s) (i.e., cycloparaffins), hydrogen, and also impurities in the presence of a catalyst, comprising platinum and a support material such as alumina, and also in the presence of an isomerization feed stream additive(s) so as to alleviate or diminish the deactivation of such catalyst.

A further object of this invention is to provide a method by which the activity or run life of an isomerization catalyst can be enhanced or essentially prolonged resulting in a substantially constant conversion, i.e, isomerization, of hydrocarbons.

A yet further object of this invention is to provide a method by which the activity of an isomerization catalyst can be enhanced during the use of such catalyst in the isomerization of hydrocarbons.

Another object of this invention is to provide a method which permits the economical isomerization of alkanes, such as normal paraffin hydrocarbons, to isoalkanes, i.e., isoparaffins, while achieving an exceptionally long and useful operating life for the associated isomerization catalyst.

The present invention, directed to a more effective method of alleviating or diminishing catalyst deactivation problems caused by, for example, the formation and accumulation of high molecular weight hydrocarbons inside the pores of such catalysts and the presence of impurities in isomerization feed streams, comprises adding an additive to the isomerization feed stream to counteract such catalyst deactivation problems. The amount of additive used is important in alleviating or diminishing catalyst deactivating effects which helps promote a substantially constant isomerization, i.e., conversion, of hydrocarbons.

The present invention provides a process which uniquely permits the isomerization of isomerizable hydrocarbons in an isomerization zone while alleviating or diminishing catalyst deactivation problems by using an additive at concentrations significantly lower than that which the prior art teaches to be acceptable or preferred. What is particularly unusual about the instant invention is the alleviating or diminishing of catalyst deactivation problems by such an inordinately low concentration of additive.

The inventive process comprises converting at least one feed hydrocarbon selected from the group consisting of alkanes (preferably normal, linear alkanes) containing about 4 carbon atoms to about 10 carbon atoms per molecule and cycloalkanes containing about 5 carbon atoms to about 10 carbon atoms per molecule to at least one product hydrocarbon isomer, e.g., an isoalkane. The isomerization feed stream comprises at least one feed hydrocarbon and hydrogen. The isomerization feed stream is contacted in a isomerization zone, which can be defined by a reactor vessel, at effective isomerization conditions with a catalyst, which preferably comprises platinum and alumina, wherein deactivation of such catalyst normally occurs in such isomerization zone. The inventive process provides for the presence of an additive comprising at least one added metal halide compound, preferably such metal halide compound is a metal chloride compound (e.g., aluminum chloride), in such isomerization feed stream in an amount sufficient to alleviate or diminish the deactivation of an isomerization catalyst and to maintain a substantially constant conversion, i.e., isomerization, of at least one feed hydrocarbon to at least one product hydrocarbon isomer at effective isomerization conditions.

Preferably, the feed hydrocarbon is a mixture of n-hexane and methylcyclopentane. The n-hexane is isomerized in the process of this invention to 2-methylpentane, 3-methylpentane, 2,2-dimethylbutane, and 2,3-dimethylbutane, with 2,2-dimethylbutane being the preferred isomer, and the methylcyclopentane is isomerized to cyclohexane. Another preferred feed hydrocarbon is n-butane which is isomerized in the process of this invention to isobutane. An organic chloride compound such as tetrachloroethylene may also be present in the isomerization feed stream of the inventive process.

The inventive process offers several benefits such as: (1) the ability to operate the process at very low hydrogen-to-hydrocarbon molar ratios (e.g., a hydrogen-to-hydrocarbon molar ratio of less than 0.5:1), (2) a substantial reduction in the amount of hydrogen used when compared to isomerization processes which do not utilize the inventive process, (3) extending the run life of the catalyst which translates into longer operating runs between catalyst regenerations, (4) the ability to operate the process at relatively low temperatures, and (5) fewer catalyst regeneration cycles which translates into safer operation, less downtime, and greater economic benefit.

Other objects and advantages of the invention will be apparent from the detailed description of the invention and the appended claims.

DETAILED DESCRIPTION OF THE INVENTION

Any straight-chain or branched alkane containing in the range of from about 4 carbon atoms to about 10 carbon atoms per molecule can be employed as feed hydrocarbon in the isomerization process of this invention. Non-limiting examples of suitable alkanes include, but are not limited to, n-butane (presently preferred), n-pentane, n-hexane (also presently preferred), 2-methylpentane, 3-methylpentane, n-heptane, 2-methylhexane, 3-methylhexane, octanes, nonanes, decanes, and the like and mixtures thereof.

Any cycloalkane containing in the range of from about 5 carbon atoms to about 10 carbon atoms per molecule can also be used as feed hydrocarbon in the process of this invention. Non-limiting examples of suitable cycloalkanes include, but are not limited to, cyclopentane, cyclohexane, methylcyclopentane, cycloheptane, methylcyclohexane, cyclooctane, methylcyclooctane, and the like and mixtures thereof.

Mixtures of alkanes and cycloalkanes (such as a preferred feed hydrocarbon of a mixture of normal hexane and methylcyclopentane), in any proportion, such as a molar ratio of alkane (e.g., normal hexane) to cycloalkane (e.g., methylcyclopentane) of from about 1:99 to about 99:1, can also be employed as feed hydrocarbon in the isomerization process of this invention. Another preferred feed hydrocarbon is a mixture of normal hexane, methylcyclopentane, and cyclohexane with a molar ratio of alkane (e.g., normal hexane) to cycloalkane (e.g., methylcyclopentane) of from about 1:90 to about 90:1.

Any catalyst effective in the isomerization of hydrocarbons can be employed as the isomerization catalyst of this invention. Alkane isomerization catalysts which catalyze the conversion of $C_4$ to $C_7$ alkanes (preferably n-hexane, n-pentane, and n-butane) to isoalkanes are well known. Preferred alkane isomerization catalysts are also commercially available, e.g., from UOP, Inc., Des Plaines, Ill., and from the Catalyst and Chemicals Division of Engelhard Corporation, Newark, N.J.

A suitable catalyst for use in the process of this invention comprises platinum and a support material, preferably an inorganic support material. Examples of suitable support materials include, but are not limited to, alumina, chlorinated alumina, silica, titania, zirconia, aluminosilicates, zinc aluminate, zinc titanate, and mixtures thereof. A preferred catalyst comprises platinum, alumina, and also aluminum chloride. Generally, the concentration of platinum in the catalyst is in the range of from about 0.01 weight percent of the catalyst to about 10 weight percent of the catalyst. Preferably, the concentration of platinum in the catalyst is in the range of from about 0.05 weight percent of the catalyst to about 1 weight percent of the catalyst, and, most preferably, the concentration of platinum in the catalyst is in the range from 0.1 weight percent of the catalyst to 0.6 weight percent of the catalyst. Generally, the surface area of the catalyst is in the range of from about 100 $m^2/g$ (measured by the Brunauer, Emmett, Teller method, i.e., BET method) to about 800 $m^2/g$. The catalyst can be fresh (unused) or it can be used and thereafter regenerated.

Another catalyst for use in the process of this invention comprises platinum and a zeolite. Examples of suitable zeolites include mordenite and also include, but are not limited to, those disclosed in Kirk-Othmer Encyclopedia of Chemical Technology, third edition, volume 15, pages 638–669 (John Wiley & Sons, New York, 1981). Preferably, the zeolite has a constraint index (as defined in U.S. Pat. No. 4,097,367, which is incorporated herein by reference) in the range of from about 0.4 to about 12, preferably in the range of from about 2 to about 9. Generally, the molar ratio of $SiO_2$ to $Al_2O_3$ in the crystalline framework of the zeolite is at least about 5:1 and can range up to infinity. Preferably the molar ratio of $SiO_2$ to $Al_2O_3$ in the zeolite framework is in the range of from about 8:1 to about 200: 1, more preferably in the range of from about 12:1 to about 100:1. Preferred zeolites include ZSM-5, ZSM-8, ZSM-11, ZSM-12, ZSM-35, ZSM-38, and combinations thereof. Some of these zeolites are also known as "MFI" or "Pentasil" zeolites. Generally, the platinum content in the zeolite-containing catalyst is the same as disclosed above for the catalyst comprising an inorganic support such as alumina.

Any suitable isomerization (also referred to as hydroisomerization) conditions can be employed in the process of this invention. Generally, the feed hydrocarbon(s) and hydrogen, preferably hydrogen gas, are premixed to provide an isomerization feed stream which is then charged to an isomerization zone, which can be defined by a reactor vessel, and contacted with the catalyst contained therein at a reaction, i.e., isomerization, temperature of at least about 80° F. Preferably the reaction temperature is in the range of from about 100° F. to about 600° F., more preferably the reaction temperature is in the range of from about 120° F. to about 575° F., and, most preferably, the reaction temperature is in the range from 140° F. to 550° F. In a preferred case of n-hexane/methylcyclopentane isomerization in the presence of hydrogen ($H_2$), the average reaction temperature in the catalyst bed is about 140° F. to about 350° F. In another preferred case of n-butane isomerization in the presence of hydrogen ($H_2$), the average reaction temperature in the catalyst bed is about 225° F. to about 450° F.

The reaction pressure can be in the range of from below atmospheric pressure upwardly to about 700 pounds per square inch absolute (psia), preferably, from about atmospheric (i.e., 14.7 psia) to about 600 psia and, most preferably, from 15 psia to 550 psia.

The feed hydrocarbon(s) can be contacted by any suitable means, method(s), or manner with the catalyst contained within the isomerization zone. The contacting step can be operated as a batch process step or, preferably, as a continuous process step. In the latter operation, a solid catalyst bed, or a moving catalyst bed, or a fluidized catalyst bed can be employed. Any of these operational modes have advantages and disadvantages, and those skilled in the art can select the one most suitable for a particular fluid and catalyst.

The flow rate at which the feed hydrocarbon(s) is charged (i.e., the charge rate of feed hydrocarbon) to the isomerization zone is such as to provide a liquid-volume hourly space velocity ("LHSV") in the range of from exceeding 0 hour$^{-1}$ upwardly to about 1000 hour$^{-1}$. The term "liquid-volume hourly space velocity", as used herein, shall mean the numerical ratio of the rate at which at least one feed hydrocarbon is charged to the isomerization zone in liters per hour divided by the liters of catalyst contained in the isomerization zone to which the at least one feed hydrocarbon is charged. The preferred LHSV of the at least one feed hydrocarbon to the reaction zone can be in the range of from about 0.25 hour$^{-1}$ to about 250 hour$^{-1}$ and, most preferably, in the range from 0.5 hours$^{-1}$ to 100 hours$^{-1}$.

Generally, the hydrogen is charged to the isomerization zone so as to provide a molar ratio of hydrogen to feed hydrocarbon(s), i.e., hydrogen-to-hydrocarbon ($H_2$:HC) molar ratio, used in the alkane isomerization process of this invention generally in the range of from about 0.01:1 to about 20:1, preferably in the range of from about 0.02:1 to about 5:1, and, most preferably, in the range of from about 0.05:1 to about 3:1.

The isomerization product, i.e., the effluent exiting the isomerization zone, can be subjected to any suitable separation means (e.g., fractional distillation) to separate the desired formed product hydrocarbon isomers (e.g., isobutane) from unconverted feed hydrocarbon(s) (e.g., n-butane) and other hydrocarbon(s) which may be present in the product. The desired product hydrocarbon isomer is thus recovered from the effluent.

In the process of this invention, impurities can also be present in the isomerization feed stream. These impurities can include, but are not limited to, sulfur compounds, water, carbon dioxide, carbon monoxide, aromatic hydrocarbons containing in the range of from about 6 carbon atoms to about 10 carbon atoms, such as, for example, benzene, toluene, and xylene, olefin hydrocarbons containing in the range of from about 2 carbon atoms to about 10 carbon atoms, and the like and combinations thereof. The amounts of these additional impurities should be small enough that the impurities do not have detrimental effects on the process of this invention. Generally, the total content of these impurities, if present, in the isomerization feed stream (on an elemental basis, based on the weight of at least one feed hydrocarbon) is in the range of from about 1 ppm impurity to about 2,000 ppm impurity (i.e., about 1 to about 2,000 parts by weight of impurity per million parts by weight of at least one feed hydrocarbon). In most cases, the impurity content is in the range of from about 10 ppm to about 200 ppm.

The amount of water in the isomerization feed stream is either essentially zero or is not to exceed about 1 ppm $H_2O$ (i.e., about 1 part by weight of $H_2O$ per million parts by weight of at least one feed hydrocarbon), and preferably should not exceed about 0.2 ppm $H_2O$. Thus, the feed hydrocarbon stream should be dried (by employing an effective desiccant, such as, but not limited to, silica gel, $CaCl_2$, alumina, molecular sieves and the like and mixtures thereof) so as to reduce the water content of the feed hydrocarbon stream to about 1 ppm $H_2O$ or less, preferably to about 0.2 ppm $H_2O$ or less, and more preferably to about 0 ppm $H_2O$ to 0.1 ppm $H_2O$. It is also necessary to use sufficiently dry hydrogen (which can be mixed with the feed hydrocarbon(s)) and to employ, if necessary, a desiccant (such as described above) to dry the hydrogen, so as to ensure that the isomerization feed stream of feed hydrocarbon(s) and hydrogen does not contain more than about 0.2 ppm $H_2O$ (based on the weight of the feed hydrocarbon portion of the isomerization feed stream).

The catalyst deactivating effect is counteracted in the process of this invention by the presence, in the isomerization feed stream, of an additive comprising a metal halide compound, preferably such metal halide compound is a metal chloride compound. The presence of the additive in the isomerization feed stream can be accomplished by adding the additive to the isomerization feed stream containing at least one feed hydrocarbon and hydrogen in an amount effective for counteracting the deactivation of the isomerization catalyst used in such process. It is also feasible to inject the additive into the feed hydrocarbon stream or into the hydrogen stream. Since both the feed hydrocarbon stream and hydrogen stream are preferably mixed, to form the isomerization feed stream, before their contact with the catalyst, the end result will be essentially the same as injecting the additive into the isomerization feed stream (containing at least one feed hydrocarbon and hydrogen).

Examples of suitable metal chloride compounds include those typically found in Friedel-Crafts catalysts, and include, but are not limited to, aluminum chloride, antimony trichloride, antimony pentachloride, tin (II) chloride, tin (IV) chloride, titanium (III) chloride, titanium (IV) chloride, zinc chloride, and the like and mixtures thereof. The presently preferred metal chloride compound is aluminum chloride. Another suitable metal compound is boron trifluoride ($BF_3$).

Generally, the effective amount of additive, preferably comprising a metal chloride compound such as aluminum chloride ($AlCl_3$), in the isomerization feed stream, i.e., the concentration of additive, preferably a metal chloride compound, in the isomerization feed stream, is in the range of from about 0.01 ppb additive (preferably a metal chloride compound, more preferably $AlCl_3$) to about 300 ppb additive (i.e., about 0.01 part by weight additive per billion parts by weight of at least one feed hydrocarbon to about 300 parts by weight additive per billion parts by weight of at least one feed hydrocarbon). Preferably, the concentration of additive in the isomerization feed stream is in the range of from about 0.05 ppb additive to about 200 ppb additive, more preferably, the concentration of additive in the isomerization feed stream is in the range of from about 0.1 ppb additive to about 100 ppb additive, and, most preferably, the concentration of additive in the isomerization feed stream is in the range from 0.1 ppb additive to 60 ppb additive.

An organic chloride compound and/or hydrogen chloride (such hydrogen chloride usually present as a result of the reaction of an organic chloride compound and hydrogen) may be also be present in the isomerization feed stream of the inventive process. Examples of suitable organic chloride compounds include, but are not limited to, carbon tetrachloride, tetrachloroethylene, hexachloroethane, 1-chlorobutane, 2-chlorobutane, 1-chloro-2-methylpropane, 2-chloro-2-methylpropane, and the like and mixtures thereof. The presently preferred organic chloride compound is tetrachloroethylene (also called perchloroethylene or PCE). The additive, preferably comprising a metal chloride compound such as aluminum chloride ($AlCl_3$), may be mixed with the organic chloride compound such as PCE to form a mixture which can be injected into the feed hydrocarbon stream, the hydrogen feed stream, or, preferably, into the isomerization feed stream of feed hydrocarbon and hydrogen.

The effective amount of such organic chloride compound, preferably perchloroethylene (PCE), in the isomerization feed stream, i.e., the concentration of organic chloride compound in the isomerization feed stream, is in the range of from about 0.01 ppm organic chloride compound to about 700 ppm organic chloride compound (i.e., about 0.01 part by weight organic chloride compound per million parts by weight of at least one feed hydrocarbon to about 700 parts by weight organic chloride compound per million parts by weight of said at least one feed hydrocarbon). Preferably, the concentration of organic chloride compound, preferably PCE, in the isomerization feed stream is in the range of from about 0.05 ppm organic chloride compound to about 600 ppm organic chloride compound, more preferably, the concentration is in the range of from about 0.1 ppm organic chloride compound to about 500 ppm organic chloride compound, and, most preferably, the concentration of organic chloride compound is in the range from 0.5 ppm organic chloride compound to 400 ppm organic chloride compound.

The amounts of additive, preferably comprising a metal chloride compound, and organic chloride compound injected into the feed hydrocarbon stream, the hydrogen feed stream, or, preferably, into the isomerization feed stream of feed hydrocarbon and hydrogen, should be such that the concentrations of the additive and organic chloride compound recited above can be maintained. The injection of the additive and organic chloride compound can be conducted continuously or intermittently, i.e., pulsed.

The additive, preferably comprising a metal chloride compound such as aluminum chloride ($AlCl_3$), and organic chloride compound are generally injected into the feed hydrocarbon stream, or into the hydrogen stream, or, preferably, into the isomerization feed stream of at least one feed hydrocarbon and hydrogen, which is passed into the isomerization zone resulting in a presence of additive and organic chloride compound in the isomerization zone. While not wishing to be bound by any particular theory, one reaction mechanism that is believed to be occurring in the inventive process which helps to prevent the deactivation of the catalyst is that high molecular weight hydrocarbons, such as $C_5$ to $C_8$ hydrocarbons, carbon, and/or coke react with the free metal chloride, such as free aluminum chloride, present in the additive instead of forming and accumulating within the pores of the catalyst, particularly at the reaction sites within the catalyst. Another possible reaction mechanism is that the additive helps prevent high molecular weight hydrocarbons and impurities (such as sulfur compounds, olefins, and aromatics) from adsorbing onto the catalyst surface at the reaction conditions of the isomerization process. One or more of these reaction mechanisms may be occurring and may even be occurring simultaneously.

The following examples are presented to further illustrate the invention and are not to be considered as unduly limiting the scope of the invention. The following examples illustrate the unexpected performance of the inventive process which alleviates or diminishes the deactivation of a catalyst while simultaneously utilizing such catalyst in the isomerization of hydrocarbons. The data presented demonstrate that the deactivation problems normally encountered by an isomerization catalyst when contacted with isomerizable hydrocarbons under isomerizable conditions can be alleviated or diminished by the novel process which helps to promote a substantially constant isomerization of hydrocarbons. This novel process has the benefit of prolonging the useful life of the isomerization catalyst over the life of such catalyst by decreasing the cyclic activation and reactivation steps of such catalyst that normally occur when the inventive process is not used.

EXAMPLE I

RUN I (Control)

In this example, lab-scale tests are described to illustrate the process of this invention.

A stainless-steel reactor (having an inner diameter of about 0.75 inch and a height of about 28 inches) was filled with a layer (about 13.5 inches high) of Alundum® (inert alumina particles having a surface area of 1 $m^2/g$ or less), a layer (about 6 inches high) of I-8 Pt/alumina isomerization catalyst (marketed by UOP, Des Plaines, Ill.; containing about 0.2 weight-% Pt, about 45 weight-% Al, about 2.9 weight-% Cl, about 0.07 weight-% Mg, about 0.07 weight-% Ti, and the remainder being essentially chemically bound oxygen and hydrogen; surface area: 195 $m^2/g$) and a top layer (about 8 inches high) of Alundum®.

The reactor contents were heated to about 280° F. in the presence of hydrogen, and a liquid alkane-containing feed (containing about 98.1 liquid-volume percent normal butane), having a Reid vapor pressure of 37.1 pounds per square inch gauge (psig), having a density of about 4.87 pounds per gallon (i.e., about 0.58 grams per cubic centimeter (g/cc)), and a molecular weight of about 58.2, from a commercial refinery of Phillips Petroleum Company was introduced into the reactor at a liquid-volume hourly space velocity of about 4 $hour^{-1}$. The alkane-containing feed also contained about 1.3 liquid-volume percent isobutane, about 0.6 liquid-volume percent neopentane, about 0.2 liquid-volume percent isopentane, about 0.6 liquid-volume percent $C_5$+ alkanes, various sulfur impurities (primarily methyl ethyl sulfide and carbon disulfide) equivalent to a total sulfur content of less than about 0.4 ppm S (on an elemental basis), and less than about 1 ppm organic fluoride. The reaction pressure was about 450 pounds per square inch gauge (psig).

To condition the catalyst, perchloroethylene (PCE), having a density of about 1.625 g/cc, was added to the liquid alkane-containing feed in an amount so as to maintain a concentration of about 83 ppm of perchloroethylene (PCE) in the liquid alkane-containing feed (i.e., about 83 parts by weight PCE per million parts by weight of at least one feed hydrocarbon) along with added hydrogen. The hydrogen was introduced in an amount so as to provide a hydrogen-to-hydrocarbon ($H_2$:HC) molar ratio in the range of from about 0.3:1 to about 2.3:1 for 28 hours. After this initial conditioning of the catalyst for 28 hours and with the exception of periodic hydrogen sweeps of the catalyst at the on-stream time periods of 43 hours, 70 hours, 125 hours, and 162 hours, the activity and deactivation of the catalyst were evaluated over a time period of about 234 hours at $H_2$:HC molar ratios in the range of from about 0.1:1 to about 0.3:1 with the concentration of PCE in the liquid alkane-containing feed maintained at about 166 ppm PCE (i.e., 166 parts by weight PCE per million parts by weight of at least one feed hydrocarbon).

The obtained isomerization product (containing isobutanes and unconverted normal butane) was analyzed by means of a gas chromatograph. The conversion, i.e., isomerization, was defined as the molar ratio of formed isobutanes in the product to all butanes (such as n-butane and isobutanes) in the product multiplied by 100 (also referred to as isobutane product ratio, % or i-$C_4$ PR, %). Since the reactor temperature was maintained at about 280° F. throughout Run I, the i-$C_4$ PR, % provided the measure of catalyst deactivation with any decrease in i-$C_4$ PR, % being an indicator of catalyst deactivation. No metal chloride additive was used in Run I. Results from Run I are summarized below in Table I.

TABLE I

| On-Stream Time Period (Hours) | i-C$_4$ PR, %* at a H$_2$:HC molar ratio of about 0.20:1 to about 0.23:1 | i-C$_4$ PR, % at a H$_2$:HC molar ratio of about 0.17:1 | i-C$_4$ PR, % at a H$_2$:HC molar ratio of about 0.12:1 |
|---|---|---|---|
| 34    | 59.4 | —    | —    |
| 76.5  | 54.9 | —    | —    |
| 82    | —    | 56.0 | —    |
| 93    | —    | 54.2 | —    |
| 113   | —    | 50.6 | —    |
| 219.5 | —    | —    | 51.1 |
| 255.5 | —    | —    | 45.9 |
| 267.5 | —    | —    | 44.9 |

*i-C$_4$ PR, % is also referred to as isobutane product ratio, % which is defined as the molar ratio of formed isobutanes in the product to all butanes (such as n-butane and isobutanes) in the product multiplied by 100.

As the data from Run I clearly demonstrate, the isomerization of butane continually decreased at various H$_2$:HC molar ratios throughout the run. At a H$_2$:HC molar ratio in the range of from about 0.20:1 to about 0.23:1, the isobutane product ratio, % (i-C$_4$ PR, %) decreased 4.5 percent from 59.4 to 54.9 during an on-stream time period of about 42.5 hours. At a H$_2$:HC molar ratio of about 0.17:1, the isobutane product ratio, % (i-C$_4$ PR, %) decreased over 5 percent from 56.0 to 50.6 during an on-stream time period of about 31 hours. At a H$_2$:HC molar ratio of about 0.12:1, the isobutane product ratio, % (i-C$_4$ PR, %) decreased over 6 percent from 51.1 to 44.9 during an on-stream time period of about 48 hours.

The i-C$_4$ PR, % consistently and steadily decreased over time at various H$_2$:HC molar ratios which indicates a consistent and steady decrease in isomerization catalyst activity.

RUN II (Invention)

To test the inventive process, Run II was conducted in the same manner as the above-described control Run I with the following exceptions. A mixture containing perchloroethylene (PCE) and an additive comprising aluminum chloride (AlCl$_3$) was added to the liquid alkane-containing feed (feed composition was the same as described above in Run I, Control) in an amount so as to maintain a concentration of about 1.8 ppb AlCl$_3$ in the liquid alkane-containing feed (i.e., about 1.8 parts by weight AlCl$_3$ per billion parts by weight of at least one feed hydrocarbon) and about 83 ppm PCE in the liquid alkane-containing feed (i.e., about 83 parts by weight PCE per million parts by weight of at least one feed hydrocarbon). Similar to Run I (Control), the catalyst was conditioned with a hydrogen-to-hydrocarbon (H$_2$:HC) molar ratio of about 2.7:1 for 24 hours using the mixture of AlCl$_3$ and PCE. Results from Run II are summarized below in Table II.

TABLE II

| On-Stream Time Period (Hours) | i-C$_4$ PR, %* at a H$_2$:HC molar ratio of about 0.20:1 | i-C$_4$ PR, % at a H$_2$:HC molar ratio of about 0.13:1 to about 0.14:1 |
|---|---|---|
| 81    | 48.5 | —    |
| 112   | 48.9 | —    |
| 159.5 | 47.9 | —    |
| 224   | 46.8 | —    |
| 248.5 | —    | 48.5 |
| 288.5 | —    | 47.3 |
| 328   | —    | 48.1 |

*i-C$_4$ PR, % is also referred to as isobutane product ratio, % which is defined as the molar ratio of formed isobutanes in the product to all butanes (such as n-butane and isobutanes) in the product multiplied by 100.

As the data from Run II clearly demonstrate, the isomerization of butane did not decrease, but remained steady at various H$_2$:HC molar ratios throughout the run. At a H$_2$:HC molar ratio of about 0.20:1, the isobutane product ratio, % (i-C$_4$ PR, %) remained steady at an average of about 48 during an on-stream time period of about 143 hours. At a H$_2$:HC molar ratio in the range of from about 0.13:1 to about 0.14:1, the isobutane product ratio, % (i-C$_4$ PR, %) remained steady at an average of about 48 during an on-stream time period of about 79.5 hours.

The i-C$_4$ PR, % was consistent and steady at various H$_2$:HC molar ratios which indicates that the activity of the isomerization catalyst was maintained by the inventive process.

Comparison of the data between Run I and Run II show that the run life of the isomerization catalyst can be extended by the novel process and that catalyst deactivation problems can be alleviated or diminished by the novel process. The difference in performance between the control run and the inventive run is certainly unexpected. One would not expect that use of an AlCl$_3$ additive at such low concentrations in the inventive process would enhance the performance of the isomerization catalyst.

EXAMPLE II

RUN III (Control)

Run III was conducted in the same manner as described above for Run I with the following exceptions. A liquid alkane-containing feed containing a mixture of normal hexane and methylcyclopentane in a 1.2:1 weight ratio and having a density of 0.8 grams per cubic centimeter (g/cc) from a commercial refinery of Phillips Petroleum Company was used in lieu of the normal butane feed used in Run I and was introduced into the reactor at a liquid-volume hourly space velocity of about 2 hour$^{-1}$ in lieu of 4 hour$^{-1}$ used in Run I. A reactor temperature of 260° F. was used in lieu of the 280° F. used in Run I. The liquid alkane-containing feed, i.e., normal hexane/methylcyclopentane feed, contained about 40.7 weight-% normal hexane, about 33.8 weight-% methylcyclopentane, about 19.1 weight-% cyclohexane, about 0.011 weight-% benzene, about 1.1 weight-% 2-methylpentane, about 4.3 weight-% 3-methylpentane, about 0.9 weight-% cyclopentane, about 0.2 weight-% normal pentane, about 0.2 weight-% 2,4-dimethylpentane, small amounts of C$_7$ and C$_8$ alkanes, and various sulfur impurities (primarily methyl ethyl sulfide and carbon disulfide) equivalent to a total sulfur content of about 0.5 ppm S (on an elemental basis). The activity and deactivation of the catalyst were evaluated over a time period of about 478 hours at a hydrogen-to-hydrocarbon ($H_2$:HC) molar ratio of about 0.16:1 with the concentration of PCE in the liquid alkane-containing feed maintained at about 368 ppm PCE (i.e., about 368 parts by weight PCE per million parts by weight of at least one feed hydrocarbon).

The obtained isomerization product was analyzed by means of a gas chromatograph. In addition to the $C_6$ conversion, i.e., $C_6$ isomerization, being defined as a weight percent of normal hexane converted (n-$C_6$ conversion, %), the $C_6$ conversion was additionally defined as the molar ratio of formed 2,2-dimethylbutane (2,2-DMB) in the product to normal hexanes in the product multiplied by 100 (also referred to as 2,2-DMB to normal hexane product ratio, % or 2,2-DMB/n-$C_6$ PR, %). Since the reactor temperature was maintained at about 260° F. throughout Run III, the n-$C_6$ conversion, % and the 2,2-DMB/n-$C_6$ PR, % provided the measure of catalyst deactivation with any decrease in n-$C_6$ conversion, % or 2,2-DMB/n-$C_6$ PR, % being an indicator of catalyst deactivation. The molar ratio of cyclohexane to methylcylclopentane was also recorded as an additional indicator of catalyst deactivation. No metal chloride additive was used in Run III. Results from Run III are summarized below in Table III.

TABLE III[1]

| On-Stream Time Period (Hours) | n-$C_6$ Conversion, % | 2,2-DMB/ n-$C_6$ PR, %[2] | CyC$_6$/MCP[3] |
|---|---|---|---|
| 48 | 57.6 | 20.9 | 1.29 |
| 72 | 61.4 | 26.8 | 1.30 |
| 95 | 57.4 | 20.9 | 1.29 |
| 384 | 39.2 | 5.7 | 1.18 |
| 408 | 35.3 | 4.9 | 1.14 |
| 455 | 26.4 | 2.6 | 1.02 |
| 526 | 31.5 | 2.3 | 1.08 |

[1]All data obtained at a $H_2$:HC molar ratio of about 0.16:1.
[2]2,2-DMB/n-$C_6$ PR, % is also referred to as 2,2-DMB to normal hexane product ratio, % which is defined as the molar ratio of formed 2,2-dimethylbutane (2,2-DMB) in the product to normal hexanes in the product multiplied by 100.
[3]Molar ratio of cyclohexane to methylcyclopentane.

As the data from Run III clearly demonstrate, the isomerization of normal hexane/methylcyclopentane continually decreased throughout the 478 hour run at a $H_2$:HC molar ratio of about 0.16:1. The n-$C_6$ conversion, %, decreased over 26 percent from 57.6 to 31.5. The 2,2-DMB/n-$C_6$ PR, % decreased over 18 percent from 20.9 to 2.3. The molar ratio of cyclohexane to methylcylcopentane (CyC6/MCP) decreased from 1.29 to 1.08.

The n-$C_6$ conversion, %, 2,2-DMB/n-$C_6$ PR, %, and the CyC6/MCP all consistently and steadily decreased over time at a $H_2$:HC molar ratio of 0.16:1 which indicates a consistent and steady decrease in isomerization catalyst activity.

RUN IV (Invention)

To test the inventive process, Run IV was conducted in the same manner as the above-described Run III with the following exceptions. A liquid alkane-containing feed containing a mixture of normal hexane and methylcyclopentane in a 1.8:1 weight ratio and having a density of 0.8 grams per cubic centimeter (g/cc) from a commercial refinery of Phillips Petroleum Company was used in lieu of the feed used in Run IV. The liquid alkane-containing feed in Run IV contained about 51.5 weight-% normal hexane, about 28.3 weight-% methylcyclopentane, about 12.6 weight-% cyclohexane, about 0.014 weight-% benzene, about 2.0 weight-% 2-methylpentane, about 5.1 weight-% 3-methylpentane, about 0.01 weight-% cyclopentane, about 0.1 weight-% normal pentane, about 0.1 weight-% 2,4-dimethylpentane, small amounts of $C_7$ and $C_8$ alkanes, and various sulfur impurities (primarily methyl ethyl sulfide and carbon disulfide) equivalent to a total sulfur content of about 0.5 ppm S (on an elemental basis).

A mixture containing perchloroethylene (PCE) and an additive comprising aluminum chloride ($AlCl_3$) was added to the liquid alkane-containing feed in an amount so as to maintain a concentration of about 57 ppb $AlCl_3$ in the liquid alkane-containing feed (i.e., about 57 parts by weight $AlCl_3$ per billion parts by weight of at least one feed hydrocarbon) and about 368 ppm PCE in the liquid alkane-containing feed (i.e., about 368 parts by weight PCE per million parts by weight of at least one feed hydrocarbon).

The activity and deactivation of the catalyst were evaluated over a time period of about 376 hours at a hydrogen-to-hydrocarbon ($H_2$:HC) molar ratio of about 0.4:1 with the concentration of $AlCl_3$ in the liquid alkane-containing feed maintained at about 57 ppb $AlCl_3$ and the concentration of PCE in the liquid alkane-containing feed maintained at about 368 ppm PCE. Results from Run IV are summarized below in Table IV.

TABLE IV[1]

| On-Stream Time Period (Hours) | n-$C_6$ Conversion, % | 2,2-DMB/ n-$C_6$ PR, %[2] | CyC$_6$/MCP[3] |
|---|---|---|---|
| 46 | 49.2 | 12 | 1.13 |
| 69 | 47.4 | 11 | 1.13 |
| 374 | 53.4 | 12 | 1.12 |
| 398 | 54.4 | 12 | 1.11 |
| 422 | 53.4 | 11 | 1.11 |

[1]All data obtained at a $H_2$:HC molar ratio of about 0.4:1.
[2]2,2-DMB/n-$C_6$ PR, % is also referred to as 2,2-DMB to normal hexane product ratio, % which is defined as the molar ratio of formed 2,2-dimethylbutane (2,2-DMB) in the product to normal hexanes in the product multiplied by 100.
[3]Molar ratio of cyclohexane to methylcyclopentane.

As the data from Run IV clearly demonstrate, the isomerization of normal hexane/methylcyclopentane remained steady throughout the 376 hour run at a $H_2$:HC molar ratio of about 0.4:1. The n-$C_6$ conversion, %, remained steady at an average of about 51.6. The 2,2-DMB/n-$C_6$ PR, % remained steady at an average of about 12. The molar ratio of cyclohexane to methylcylcopentane (CyC6/MCP) remained steady at an average of about 1.12.

The n-$C_6$ conversion, %, 2,2-DMB/n-$C_6$ PR, %, and the CyC6/MCP all remained consistent and steady over time at a $H_2$:HC molar ratio of 0.4:1 which indicates that the activity of the isomerization catalyst was maintained by the inventive process.

Comparison of the data between Run III and Run IV shows that the run life of the isomerization catalyst can be extended by the novel process and that catalyst deactivation problems can be alleviated or diminished by the novel process. The drastically improved performance of the inventive run over the control run is certainly unexpected. One would not expect that use of an $AlCl_3$ additive at such low concentrations in the inventive process would enhance the performance of the isomerization catalyst.

EXAMPLE III

The following example demonstrates that the inventive process can be used to provide a substantial increase in $C_6$ conversion, i.e., $C_6$ isomerization, defined as the molar ratio of formed 2,2-dimethylbutane (2,2 DMB) in the product to normal hexanes in the product multiplied by 100 (also referred to as 2,2-DMB to normal hexane product ratio, % or 2,2-DMB/n-$C_6$ PR, %), at a substantially decreased hydrogen-to-hydrocarbon molar ratio and at a substantially decreased aluminum chloride concentration. Thus, the example demonstrates that catalyst deactivation problems can still be alleviated or diminished even when the inventive process utilizes substantially decreased hydrogen-to-hydrocarbon molar ratios and aluminum chloride concentrations. The example also demonstrates the effectiveness of the inventive process at the high severity of a low hydrogen-to-hydrocarbon molar ratio.

RUN V (Invention)

Run V was conducted in the same manner as Run IV, described above in Example II, except that the hydrogen-to-hydrocarbon molar ratio was reduced from about 0.4:1 to about 0.1:1 and the mixture containing perchloroethylene (PCE) and an additive comprising aluminum chloride ($AlCl_3$) added to the liquid alkane-containing feed, was reduced in amount so as to maintain a concentration of about 27 ppb $AlCl_3$ in the liquid alkane-containing feed (i.e., about 27 parts by weight $AlCl_3$ per billion parts by weight of at least one feed hydrocarbon) instead of the about 57 ppb $AlCl_3$ in the liquid alkane-containing feed used in Run IV (i.e., about 57 parts by weight $AlCl_3$ per billion parts by weight of at least one feed hydrocarbon) while the PCE concentration remained the same as Run IV at about 368 ppm PCE in the liquid alkane-containing feed (i.e., about 368 parts by weight PCE per million parts by weight of at least one feed hydrocarbon).

The liquid alkane-containing feed composition was the same as described above for Run IV and was introduced into the reactor at a liquid-volume hourly space velocity of about 2 hours$^{-1}$ which was the same as Run IV. The activity and deactivation of the catalyst were evaluated over a time period of about 197 hours at a hydrogen-to-hydrocarbon ($H_2$:HC) molar ratio of about 0.1:1 with the concentration of $AlCl_3$ in the liquid alkane-containing feed maintained at about 27 ppb $AlCl_3$ and the concentration of PCE in the liquid alkane-containing feed maintained at about 368 ppm PCE. Results from Run V are summarized below in Table V.

TABLE V[1]

| On-Stream Time Period (Hours) | n-$C_6$ Conversion, % | 2,2-DMB/ n-$C_6$ PR, %[2] | CyC$_6$/MCP[3] |
|---|---|---|---|
| 1160 | 62.6 | 29 | 1.31 |
| 1185 | 64.2 | 36 | 1.31 |
| 1209 | 64.9 | 32 | 1.31 |
| 1357 | 65.0 | 36 | 1.31 |

[1]All data obtained at a $H_2$:HC molar ratio of about 0.1:1.
[2]2,2-DMB/n-$C_6$ PR, % is also referred to as 2,2-DMB to normal hexane product ratio, % which is defined as the molar ratio of formed 2,2-dimethylbutane (2,2-DMB) in the product to normal hexanes in the product multiplied by 100.
[3]Molar ratio of cyclohexane to methylcyclopentane.

As the data from Run V clearly demonstrate, the isomerization of normal hexane/methylcyclopentane remained steady throughout the 197 hour run at a $H_2$:HC molar ratio of about 0.1:1. The n-$C_6$ conversion, %, remained steady at an average of about 64.2. The 2,2-DMB/n-$C_6$ PR, % remained steady at an average of about 33. The molar ratio of cyclohexane to methylcylcopentane (CyC6/MCP) remained steady at an average of about 1.31.

The n-$C_6$ conversion, %, 2,2-DMB/n-$C_6$ PR, %, and the CyC6:MCP all remained consistent and steady over time at a $H_2$:HC molar ratio of about 0.1:1 which indicates that the activity of the isomerization catalyst was maintained by the inventive process.

Comparison of the data between Run III and Run V show that the run life of the isomerization catalyst can be extended by the novel process and that catalyst deactivation problems can be alleviated or diminished by the novel process. Further, the data demonstrates the effectiveness of the inventive process at the high severity of a low $H_2$:HC molar ratio of about 0.1:1. Even at a substantially decreased hydrogen-to-hydrocarbon molar ratio (the hydrogen-to-hydrocarbon molar ratio was reduced from about 0.4:1 (Run IV) to about 0.1:1) and at a substantially decreased aluminum chloride concentration in the liquid alkane-containing feed (the $AlCl_3$ concentration in the liquid alkane-containing feed was reduced from about 57 ppb (Run IV) to about 29 ppb), the inventive process was still effective in alleviating or diminishing catalyst deactivation problems.

The difference in performance between the control run and the inventive run is certainly unexpected. One would not expect that use of an $AlCl_3$ additive at such low concentrations in the inventive process would enhance the performance of the isomerization catalyst.

The results shown in the above examples clearly demonstrate that the present invention is well adapted to carry out the objects and attain the ends and advantages mentioned as well as those inherent therein.

Reasonable variations, modifications and adaptations for various conditions and reactants can be made within the scope of the disclosure and the appended claims without departing from the scope of this invention.

What is claimed is:

1. A process for converting at least one feed hydrocarbon selected from the group consisting of alkanes containing in the range of from about 4 carbon atoms to about 10 carbon atoms per molecule and cycloalkanes containing in the range of from about 5 carbon atoms to about 10 carbon atoms per molecule to at least one product hydrocarbon isomer, wherein an isomerization feed stream, which comprises said at least one feed hydrocarbon and hydrogen, is contacted in an isomerization zone at effective isomerization conditions with a catalyst, wherein deactivation of said catalyst occurs in said isomerization zone, and further wherein said process comprises the presence of an additive in said isomerization feed stream in a concentration in the range of from about 0.01 part by weight of said additive per billion parts by weight of said at least one feed hydrocarbon (about 0.01 ppb additive) to about 300 parts by weight of said additive per billion parts by weight of said at least one feed hydrocarbon (about 300 ppb additive) and further wherein said additive comprises a metal chloride compound selected from the group consisting of aluminum chloride, antimony trichloride, antimony pentachloride, tin (II) chloride, tin (IV) chloride, titanium (III) chloride, titanium (IV) chloride, zinc chloride, and mixtures thereof.

2. A process according to claim 1, wherein said concentration of said additive in said isomerization feed stream is in the range of from about 0.05 part by weight of said additive per billion parts by weight of said at least one feed hydrocarbon (about 0.05 ppb additive) to about 200 parts by weight of said additive per billion parts by weight of said at least one feed hydrocarbon (about 200 ppb additive).

3. A process according to claim 1, wherein said metal chloride compound is aluminum chloride.

4. A process according to claim 3, wherein an organic chloride compound is present in said isomerization feed stream.

5. A process according to claim 4, wherein said organic chloride compound is selected from the group consisting of carbon tetrachloride, tetrachloroethylene (also called perchloroethylene or PCE), hexachloroethane, 1-chlorobutane, 2-chlorobutane, 1-chloro-2-methylpropane, 2-chloro-2-methylpropane, and mixtures thereof.

6. A process according to claim 5, wherein the concentration of said organic chloride compound in said isomerization feed stream is in the range of from about 0.01 part by weight of said organic chloride compound per million parts by weight of said at least one feed hydrocarbon (about 0.01 ppm organic chloride compound) to about 700 parts by weight of said organic chloride compound per million parts by weight of said at least one feed hydrocarbon (about 700 ppm organic chloride compound).

7. A process according to claim 6, wherein the concentration of said organic chloride compound in said isomerization feed stream is in the range of from about 0.05 part by weight of said organic chloride compound per million parts by weight of said at least one feed hydrocarbon (about 0.05 ppm organic chloride compound) to about 600 parts by weight of said organic chloride compound per million parts by weight of said at least one feed hydrocarbon (about 600 ppm organic chloride compound).

8. A process according to claim 7, wherein said organic chloride compound is tetrachloroethylene (also called perchloroethylene or PCE).

9. A process according to claim 1, wherein said alkanes is selected from the group consisting of n-butane, n-pentane, n-hexane, 2-methylpentane, 3-methylpentane, n-heptane, 2-methylhexane, 3-methylhexane, octanes, nonanes, decanes, and mixtures thereof.

10. A process according to claim 9, wherein said alkanes is selected from the group consisting of n-butane and n-hexane.

11. A process according to claim 1, wherein said cycloalkanes is selected from the group consisting of cyclopentane, cyclohexane, methylcyclopentane, cycloheptane, methylcyclohexane, cyclooctane, methylcyclooctane, and mixtures thereof.

12. A process according to claim 11, wherein said cycloalkanes is selected from the group consisting of methylcyclopentane and cyclohexane.

13. A process according to claim 1, wherein said at least one feed hydrocarbon is n-butane.

14. A process according to claim 1, wherein said at least one feed hydrocarbon is a mixture of said alkanes and said cycloalkanes.

15. A process according to claim 1, wherein said at least one feed hydrocarbon is a mixture of normal hexane and methylcyclopentane.

16. A process according to claim 15, wherein the molar ratio of said normal hexane to said methylcyclopentane in said mixture is in the range of from about 1:99 to about 99:1.

17. A process according to claim 1, wherein said at least one feed hydrocarbon is a mixture of normal hexane, methylcyclopentane, and cyclohexane.

18. A process according to claim 17, wherein the molar ratio of said normal hexane to said methylcyclopentane in said mixture is in the range of from about 1:90 to about 90:1.

19. A process according to claim 1, wherein said feed stream comprises impurities selected from the group consisting of sulfur compounds, water, carbon dioxide, carbon monoxide, aromatic hydrocarbons containing in the range of from about 6 carbon atoms to about 10 carbon atoms, olefin hydrocarbons containing in the range of from about 2 carbon atoms to about 10 carbon atoms, and combinations thereof.

20. A process according to claim 1, wherein said at least one product hydrocarbon isomer is recovered from the effluent exiting said isomerization zone.

21. A process according to claim 1, wherein said effective isomerization conditions comprise:

a reaction temperature in the range of from about 100° F. to about 600° F., a pressure in the range of from below atmospheric pressure upwardly to about 700 pounds per square inch absolute, a charge rate of said at least one feed hydrocarbon in the range of from exceeding 0 hours$^{-1}$ upwardly to about 1000 hours$^{-1}$, and a molar ratio of said hydrogen to hydrocarbon of said at least one feed hydrocarbon in the range of from about 0.01:1 to about 20:1.

22. A process according to claim 1, wherein said concentration of said additive in said isomerization feed stream is maintained by continuously injecting said additive into said isomerization feed stream.

23. A process according to claim 1, wherein said concentration of said additive in said isomerization feed stream is maintained by intermittently injecting said additive into said isomerization feed stream.

24. A process according to claim 1, wherein said catalyst comprises platinum and an inorganic support material.

25. A process according to claim 1, wherein said catalyst comprises platinum and a zeolite.

26. A process according to claim 24, wherein the concentration of said platinum in said catalyst is in the range of from about 0.01 weight percent of said catalyst to about 10 weight percent of said catalyst.

27. A process according to claim 25, wherein the concentration of said platinum in said catalyst is in the range of from about 0.01 weight percent of said catalyst to about 10 weight percent of said catalyst.

* * * * *